United States Patent [19]

Tsibris

[11] 4,162,355

[45] Jul. 24, 1979

[54] COPOLYMERS OF (A) AMINIMIDES AND (B) VINYL PENDANT PRIMARY HALOMETHY MONOMERS USEFUL FOR AFFINITY CHROMATOGRAPHY

[75] Inventor: John C. M. Tsibris, Gainesville, Fla.

[73] Assignee: Board of Regents, for and on behalf of the University of Florida, Tallahassee, Fla.

[21] Appl. No.: 701,410

[22] Filed: Jun. 30, 1976

[51] Int. Cl.$^2$ .................. C08F 4/04; C08F 14/02; C08F 20/52; C08F 214/02

[52] U.S. Cl. .................. 526/293; 210/31 C; 427/214; 427/221; 427/340; 526/218; 525/380; 525/382

[58] Field of Search ............... 526/293, 304, 307, 312

[56] References Cited

U.S. PATENT DOCUMENTS

| | | | |
|---|---|---|---|
| 3,664,990 | 5/1972 | Slagel | 526/307 |
| 3,715,343 | 2/1973 | Slagel et al. | 526/293 |
| 3,728,387 | 4/1973 | Freis et al. | 526/304 |
| 3,803,220 | 4/1974 | Gasman | 526/304 |
| 3,843,566 | 10/1974 | Barrett | 526/293 |
| 3,872,067 | 3/1975 | Harris | 526/293 |
| 3,969,298 | 7/1976 | Gasman | 526/307 |
| 3,985,807 | 10/1976 | Grimm et al. | 526/304 |
| 4,005,055 | 1/1977 | Miron et al. | 526/312 |

Primary Examiner—Herbert J. Lilling
Attorney, Agent, or Firm—Dennis P. Clarke

[57] ABSTRACT

A polymer suitable for use in affinity chromatography comprising a polymer of an aminimide and a vinyl compound having at least one pendant halo-methyl group and the said polymer wherein an amine ligand which affords sites for binding in affinity chromatography is coupled to the polymer by reaction with a portion of the pendant halo-methyl groups and the remainder of said pendant halo-methyl groups are reacted with an amine containing a pendant hydrophilic group.

The invention also comprises a method of coating a substrate with the above polymer and a method of fractionating mixtures by affinity chromatography employing the above polymer as an adsorbent.

2 Claims, No Drawings

COPOLYMERS OF (A) AMINIMIDES AND (B) VINYL PENDANT PRIMARY HALOMETHY MONOMERS USEFUL FOR AFFINITY CHROMATOGRAPHY

BACKGROUND OF THE INVENTION

1. Field of the Invention

Affinity chromatography has recently become valuable in research involving biological materials. It is particularly valuable for the purification of various biologically active molecules such as small ligands, proteins, nucleic acids and enzymes, etc. In affinity chromatography, a substrate is immobilized on the support during the chromatography. By utilizing a column of the immobilized substrate, materials having affinity or binding specificity for the compounds bonded to the stationary phase can be separated from other materials in a mixture.

Heretofore, complex polysaccharide materials such as agarose beads, etc., were employed in affinity chromatography. A suitable ligand is bonded to the polysaccharide matrix through one of a variety of methods. By passing a liquid mixture containing molecules which having a binding affinity for the ligand on the column, the materials which have affinity for the ligand will be preferentially bound to the insoluble and stationary substrate. The bound material may then be eluted by passing a solution through the column which reduces the binding affinity of the material for the ligand.

The insoluble or stationary phase material should preferably interact very weakly with the materials to be separated so as to minimize non-specific adsorption. The insoluble material should ideally comprise uniform, spherical particles exhibiting good flow and mechanical properties and which retain their insoluble characteristics after conjugation with a particular ligand. The substrate should be mechanically and chemically stable under all conditions of affinity chromatography methods. In addition, the insoluble phase should form a loose, porous network which permits uniform flow of the mixture to be fractionated through the entire structure.

The most common material utilized today as the stationary substrate for affinity chromatography is agarose or other polysaccharide materials. These materials, however, do not possess ideal flow characteristics and tend to pack under pressure into a solid mass making uniform flow of the mixture to be fractionated therethrough difficult. In addition, the polysaccharide materials employed today are not sufficiently stable under all conditions employed in liquid chromatography of biological materials thereby shortening their useful life span.

One particularly troublesome disadvantage associated with polysaccharide supports derives from the fact that it is usually necessary to employ cyanogen halides to bond the ligand thereto. The utilization of cyanogen halides, however, results in the formation of isourea groups in the substrate thereby giving rise to an anion-exchange capacity therein. The presence of these isourea groups renders the substrate non-useful for the purification *by affinity chromatography* of acidic enzymes (i.e., those with an isoelectric point of 4-6). Cyanogen halide treated polysaccharide supports are also incompatible with organic solvents such as acetone, chloroform and benzene and are subject to microbioal attack.

A further disadvantage associated with polysaccharide supports is that they are unsuitable for use in high pressure liquid chromatography applications. In these methods, the material to be fractionated as well as the elution media, etc., are forced through the column under high pressure thereby greatly shortening the overall separation time. The polysaccharide supports are totally unsuitable for use in these applications since they tend to pack together into an impermeable mass under pressure. The use of high pressure techniques would be especially advantageous in the purification of biologically active molecules such as enzymes, etc. due to the instability of most biologically active molecules. Most gravitational flow affinity chromatography methods require long periods of time, i.e., 1–3 days, to complete, thereby rendering them unsuitable for the treatment of highly unstable enzymes, etc. Solid supports, such as glass beads, would appear to be ideally suited for absorbent media in affinity chromatography methods, particularly those operated under high pressures. Their great rigidity and strength characteristics would render them ideal for packing chromatographic columns.

Workers active in the field, however, have indicated that glasses are unsuitable. Lowe et al ("Affinity Chromatography", John Wiley, London, 17, 1974) state that glasses absorb strongly basic and some neutral proteins and that this presents a serious hazard to their widespread use in selective functional purifications. Zaborsky ("Separation and Purification Methods", Vol. 3, 1 (1974)) states that glass supports are "soluble" to some extent at high pH. In addition, no satisfactory method has been proposed for coating glass beads with ligand-containing materials suitable for utilization in affinity chromatography.

It is an object of the present invention to provide intermediates, copolymers containing suitable ligands and insoluble, stationary phase substrates bonded to said copolymers for utilization in affinity chromatography methods.

These and other more widespread objects will become apparent from the following description of the invention.

2. Description of the Prior Art

In addition to the above-noted publications, the following reference describes various aspects of the art of affinity chromatography:

Cuatrecasas et al, "Advances in Enzymology", 36, 29 (1972)

U.S. Pat. No. 3,715,343 to Slagel et al disclose various polymers of vinyl aminimides.

SUMMARY OF THE INVENTION

This invention relates to a polymer suitable for use in affinity chromatography comprising a polymer of (1) at least one aminimide of the structural formula:

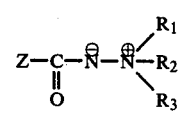

wherein:

$R_1$ and $R_2$ are the same or different and represent lower alkyl;

$R_3$ represents an organic group, preferably lower alkyl, hydroxyalkyl, phenyl, or polyoxypropylene; and Z represents the residue of a polymerizable vinyl compound, e.g., acrylic, methacrylic or crotonic acids, and (2) a vinyl compound having at least one pendant halomethyl group.

The invention further relates to the above polymer wherein an amine ligand which affords sites for binding in affinity chromatography is coupled to said polymer by reaction of said primary amine with a portion of the pendant halomethyl groups and, optionally, the remainder of said pendant halomethyl groups are reacted with an amine containing a pendant hydrophilic group, e.g., carboxyl, amino, hydroxyl, sulfonyl, phosphonyl, sulfido, etc.

The invention further relates to a system suitable for affinity chromatography comprising a column of the above polymer or a support material coated with the above-described ligand containing polymer.

The invention further relates to a method of coating a support material with a polymer, said polymer being suitable for use in affinity chromatography, comprising contacting a support material with a solvent solution of the above ligand containing polymer, removing said solvent and then contacting said coated support with a non-solvent for the final product which contains an amine having a pendant hydrophilic group, whereby said amine reacts with the remainder of said halomethyl groups and enhances the bond between said polymer and said support.

The invention further relates to an affinity chromatography method wherein the adsorbent employed comprises the above polymer or a support coated with the said polymer.

The invention further relates to various intermediate compounds and compositions useful in the preparation of the adsorbent polymers.

DESCRIPTION OF THE PREFERRED EMBODIMENTS

The basic aminimide copolymers suitable for formation of the ligand containing polymers useful in affinity chromatography are, for the most part, soluble in conventional organic solvents. This solubility in organic solvents renders the coupling of the ligand thereto relatively easy to accomplish. The neutralization of the remaining halomethyl groups after formation of the ligand containing polymer by reaction with a primary amine containing a hydrophilic group renders the resulting polymer insoluble in organic solvents but wettable by water. This is a highly advantageous property since the substrate remains insoluble and stationary during the separation process but highly amenable to elution with aqueous solutions. The unique advantages associated with the modified polymers are excellent chemical stability, mechanical strength, good flow rates, compatibility with organic solvents facilitating synthesis and removal of unreacted ligands, weak ion-exchange properties near neutrality.

It is to be understood, however, that the polymers containing only the ligand and whose remaining halomethyl groups are not neutralized also find utility in affinity chromatography methods.

Generally, the basic polymer according to the invention comprises a polymer of at least one aminimide of the structural formula:

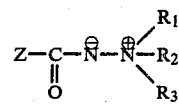

wherein:

$R_1$ and $R_2$ are the same or different and represent lower alkyl;

$R_3$ represents an organic group, preferably lower alkyl, hydroxyalkyl, phenyl, or polyoxypropylene;

Z represents the residue of a polymerizable vinyl compound, e.g., acrylic, methacrylic or crotonic acids, and a vinyl compound having at least one pendant halomethyl group.

Among the preferred aminimides are: 1,1-dimethyl-1-(2-hydroxyoctyl)amine methacrylimide, 1,1-dimethyl-1-(2-hydroxypropyl)amine methacrylimide and 1,1-dimethyl-1-(2-polyoxypropylene)amine methacrylimide.

It is to be understood, however, that any of the polymerizable aminimides may be employed to form the polymers of the invention. In this regard, $R_3$ in the above structural formula may be the residue of any organic group.

Any vinyl compound containing at least one pendant halomethyl group can be copolymerized with the aminimide to form the basic polymer. Preferred vinyl compounds include:

The halomethyl styrenes, preferably a mixture comprising 40% p- and 60% m- chloromethyl styrene; and

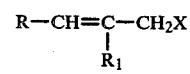

wherein R and $R_1$ can be the same or different and represent hydrogen or lower alkyl.

The aminimides may be prepared by reacting the corresponding substituted hydrazine with an appropriate epoxide and vinyl group containing carboxylic acid ester. The procedure set forth in U.S. Pat. Nos. 3,485,806 and 3,715,343 may be employed to prepare the aminimide monomer. Generally speaking, the reaction conditions required for completion of the reaction are not critical. Any of the polymerizable aminimides described in the above U.S. Patents may be utilized in the preparation of the polymers of the invention.

The polymer is then contacted with a suitable amine ligand which affords sites for binding in the contemplated affinity chromatography process. The ligand is covalently coupled to the polymer by reaction of the amine groups thereof with a portion of the pendant halomethyl groups. As will be apparent to those skilled in the art, it is necessary only to couple a small number of ligand groups to the copolymer. The presence of an excess of binding site ligands is disadvantageous for several reasons. Firstly, the mixtures to be fractionated contain only nanomolar to millimolar concentrations of the biological molecules to be separated. Secondly, the presence of too many ligands will render the polymer non-specific and result in the adsorption of undesired molecules. Generally, the resulting modified polymer will contain from about 1 to about 100 micromoles of ligand per gram, dry weight, of aminimide polymer, preferably 1 to about 40 micromoles per gram, dry weight. It is to be understood, however, that the amount of ligand present in the polymer will depend to a large degree upon the contemplated affinity chromatography method.

Suitable amine ligands include any primary or secondary amine analog of a substrate which may be separated from mixtures utilizing affinity chromatography techniques. The present invention is particularly suited, although not limited, to the separation of enzymes from their mixtures. It is to be understood, however, that virtually any organic molecule susceptible to affinity chromatographic separation methods may be fractionated according to the present invention by coupling to the aminimide polymer an amine analog of the molecule.

Preferred amine analogs or ligands include:

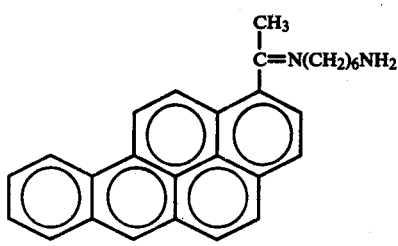

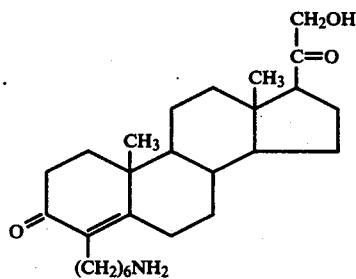

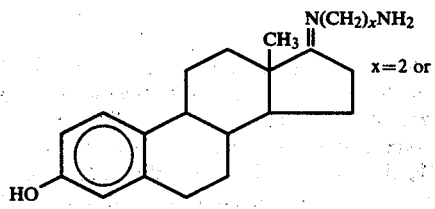

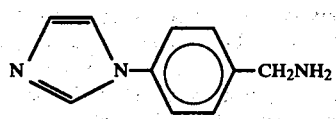

-continued

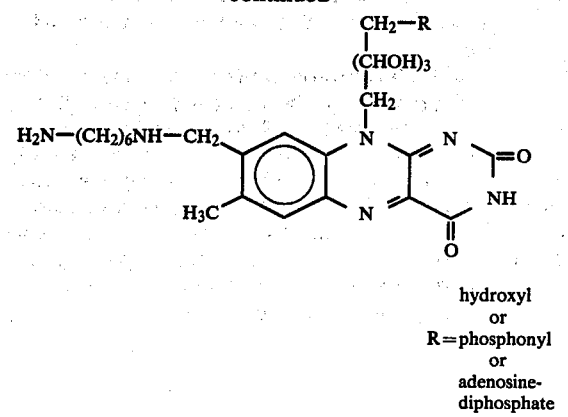

hydroxyl
or
R = phosphonyl
or
adenosine-
diphosphate

The resulting modified aminimide polymer is still relatively soluble in organic solvents. To render the polymer insoluble in organic solvents but wettable with water, the remaining pendant halomethyl groups may be reacted with a primary or secondary amine which also contains a pendant hydrophilic group such as hydroxyl, carboxyl, amino, sulfonyl, phosphony, sulfido, etc.

Preferred hydrophilic group containing amines are monoethanolamine or

where $x = 2-10$, Y may be OH, $NH_2$, COOH, $SO_3H$, $PO_3H$, SH and R is lower alkyl or H.

The invention also includes a suitable support for affinity chromatography coated with the above-described aminimide polymers.

Preferred among the supports for affinity chromatography are glass micro-beads due to their mechanical strength, good packing properties, and relative stability. The provision of the modified aminimide polymers of the present invention enables the coating of supports such as glass beads with a material which facilitates greatly the affinity chromatography methods. Other support materials include stainless steel, nickel, teflon-micro particles and porous glass beads.

The invention also includes a highly advantageous process for coating the support with the modified polymer. Since the polymer containing the amine ligand coupled through the halomethyl group is still solbule in many organic solvents, an organic solvent solution of the ligand-containing polymer is contacted with the support and the solvent removed, e.g., by evaporation, vacuum distillation, etc., to produce a coated support. The latter is then contacted with a non-solvent for the ultimate polymer, said solvent containing an amine having the pendant hydrophilic groups whereby the remainder of the halomethyl groups are coupled therewith to produce an insoluble phase containing the ultimate polymer. Ideally, a tertiary amine such as triethylamine is included in the final solution to bind the hydro halide released during the process.

Suitable solvents for the various steps are readily ascertainable by those skilled in the art and will depend to a large degree upon the particular amine ligand and hydrophilic group containing amine employed. Suitable solvents for the coating step include benzene, chloroform, dichloromethane, dimethylformamide, dimethylsulfoxide or other solvents containing no active hydrogen amine.

The final insolubilization of the coating and coupling with the hydrophilic group containing amine greatly strengthens the adherence of the ultimate polymer to the support material. Suitable non-solvents for the ultimate polymer include diethylether, n-pentane, hexanes, petroleum ether (30°-60° C. b.p.) and mixtures thereof.

The following is a reaction scheme which depicts the formation of an animimide copolymer containing a benzo[a]pyrene amine ligand and monoethanolamine as a hydrophilic group containing primary amine coupling agent:

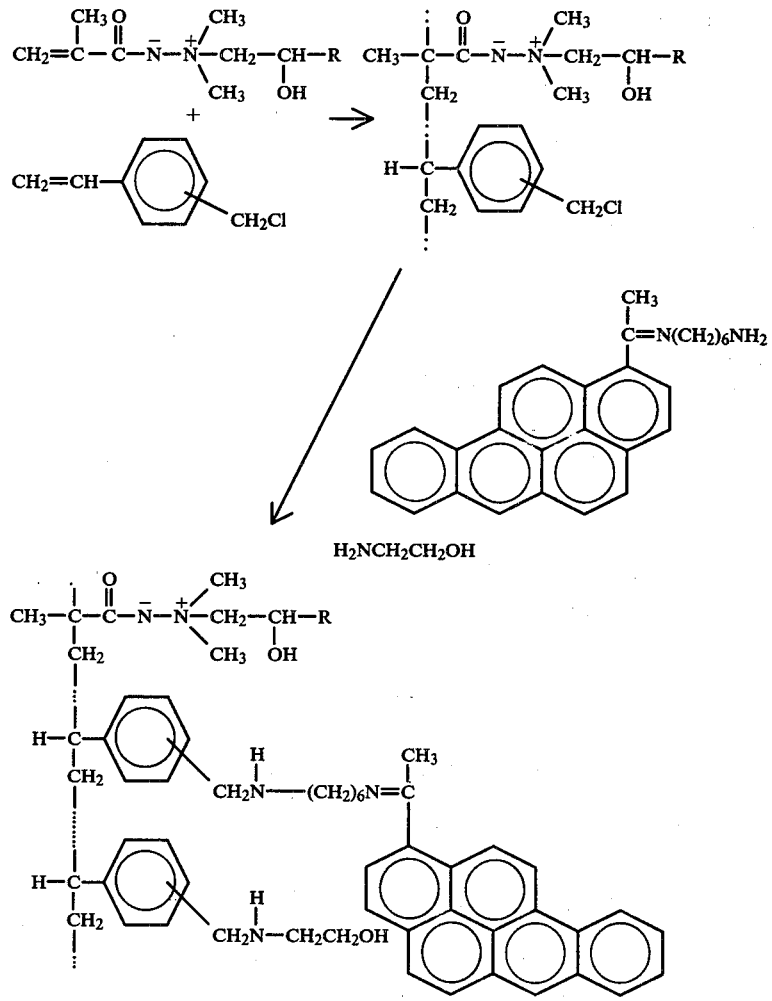

The aminimide polymer, unlike all known supports for affinity chromatography, is initially soluble in organic solvents. The coupling to the polymer of the amine ligand can be acheived directly without prior activation of the resin which cyanogen halides, etc., and in a homogenous solution. The remaining halomethyl groups on the resin are then reacted with monoethanolamine to render the polymer insoluble in organic solvents but wettable with water.

The resulting benzo[a]pyrene analog containing aminimide polymer is useful for purifying enzyme mixtures containing enzymes known to metabolize benzo[a]pyrene.

The following example illustrates an affinity chromatography system employing the above-modified polymer.

EXAMPLE 1

Preparation of Amimimide Polymer 0.63 moles of 1,1-dimethyl-1-(2-hydroxyoctyl)amine methacrylimide and 0.37 moles chloromethylstyrene (40% p- and 60% m-) were mixed with m-xylene. Polymerizaion was initiated by heating to 90° in the presence of $\alpha,\alpha'$-azo bis isobutyronitrile free radical initiator and was carried out for five hours under $N_2$. The product was precipitated twice from diethylether and shown (by elem. analysis) to contain 2.15 mequ "benzyl" chloride per g dry resin. 1-acetyl-benzo[a]pyrene was made from $^{14}C$-benzo[a]pyrene according to Windaus and Raichle Ann. 537, 157-170 (1939). The twice recrystallized product had: mp 189°-191°; $\nu_{c=o}$ at 6.0 $\mu$m ($CHCl_3$); NMR ($C^2HCl_3$)methyl 2.85 ppm from TMS standard and was estimated 97% pure by counting the $^{14}C$-content of TLC spots; yield 50%. The amine ligand of the above scheme was made according to the method described by Weingarten et al, *J. Org. Chem.* 32, 3246-49 (1967) using excess 1,6-hexanediamine, isolated and had $\nu_{C=N}$ at 6.08 $\mu$m ($CHCl_3$); according to specific radioactivity and NMR spectra in the presence or absence of $^2H_2O$ it was ca.90% pure; yield 80%.

Coupling of ligand to the polymer was carried out in benzene in presence of triethylamine (a 6-fold molar excess of ligand is added over the desired benzo[a]pyrene content in polymer) at 40° C. for 3 hours. Then monoethanolamine (5-fold molar excess relative to starting "benzyl" chloride) was added and the mixture stirred for 30 hours at 40° C. The polymer was filtered and washed with benzene, methanol-chloroform (1:4 V/V), ether, ethanol, buffer solution, ethanol, chloroform and ether. The yield was 80–87% and ligand content (6 μmoles benzo[a]pyrene g dry resin) was estimated from measurements of radioactivity by scintillation counting. One g dry resin gave approximately 4 ml wet resin. Before packing a column, the dry resin was wetted with ethanol and washed on a filter with buffer. After use the resin was washed, treated with protease, washed with water, organic solvents and stored in the dark.

Preparation of Enzymes Metabolizing Benzo[a]pyrene

Long Evans male rats, (60–70 g) were injected intraperitoneally once a day for three days with 3-methylcholanthrene (25 mg/kg) in corn oil and fasted for 18 hours before decapitation. Each liver was perfused with 50 ml cold saline solution. Microsomes obtained according to Lu et al, *J. Biol. Chem.*, 247, 1727–1734 (1972), were sonicated in the absence of detergent and applied on a Sephadex G-10 column equilibrated with 0.33 M Tris-Cl pH 7.7. All red fractions eluted with the equilibrating buffer were combined and treated with sodium cholate (1 mg cholate per mg protein) and centrifuged at 105,000 xg for 1 hour. The supernatant solution was dialyzed anaerobically at 4° for 48 hours against many changes of 50 mM potassium phosphate pH 7.5 and a final change of the same buffer containing 20% blycerol (which will be referred to as buffer) and was applied on a buffer-equilibrated animide column (1.5×13 cm). Columns were run at 8°–9° with flow rates of 0.5 ml·min$^{-1}$ using a 1 m hydrostatic head pressure, and 10–12 ml fractions were collected.

Partially purified cytochrome P-450 reductase (free of cytochrome P-450) from phenobarbital induced rat liver microsomes was eluted with 0.12% Renex-690-KCl from DEAE-Sephadex A-25 (Dignam, J. D. and Strobel, H. W. (1975) *Biochem. Biophys. Res. Commun.* 63, 845–852).

Cytochrome P-448, cytochrome P-420 (Omura, T. and Sato, R. (1964), *J. Biol. Chem.* 239, 2379–2385) and protoheme (Appleby, C. A. and Morton, R. K. (1959) *Biochem. J.* 73, 539–550) were determined according to indicated methds and protein by a microbiuret or modification of the Lowry method (Want, C. S. and Smith, R. L. (1975) *Anal. Biochem.* 63, 414–417) using bovine serum albumin as standard.

P-448 induced in rat liver with 3-methylcholanthrene differs catalytically and spectrally from P-450, the terminal oxidase of monooxygenases which are induced with phenobarbital and catalyze the incorporation of molecular oxygen to drugs, steroids, hydrocarbons, etc. P-446 can be solubilized from microsomes, has been extensively purified and in a reconstituted system, namely, after addition of the other two required components—P-448 reductase and lipid, it catalyzes the production of benzo[a]pyrene-arene oxides which are presently believed to be the ultimate carcinogenic forms of polycyclic hydrocarbons.

The present example provides a polymer containing a covalently bound water-insoluble analog of benzo[a]pyrene which is used to separate and purify the cytochrome P-448 fractions and provide enzyme preparations which can metabolize benzo[a]pyrene. These P-448 preparations yield different amounts of two groups of benzo[a]pyrene phenols.

Upon addition of UDP-glucuronate to the three P-448 reconstituted systems water soluble BP-metabolites, presumably glucuronides are produced at the expense of BP-quniones and BP-phenols. Subsequently, treatment of these metabolites with β-glucuronidase or mild acid treatment releases amounts exclusively Bp-quinones.

Table I summarizes the elution of P-448, P-420 (the inactive form(s) of P-448) and protoheme (which would also include cytochrome b$_5$) from the unsubstituted (aminimide copolymer described above reacted only with monoethanolamine, AID-EA) column. It can be concluded that, (a) the polymer treated with monoethanolamine only has no affinity for P-448 and P-420 and that 60% of P-448 has probably been inactivated to P-420 on the column since there is 220% yield of eluted P-420; (b) KCl elution of only 3% P-448 and quantitative elution of hen ovalbumin, pl=4.8, confirms that this polymer has negligible anion-exchange properties, and (c) the recover of only 40–60% protein and protoheme indicates the affinity of some proteins, extracted from microsomes with Na-cholate, for the hydrophoblic regions of the polymer.

Table I.

| | | | | | | | | | Protoheme (pyridine hemochromogen) | |
|---|---|---|---|---|---|---|---|---|---|---|
| | Volume | Protein | | Cytochrome P-448+ | | | P-420+ | | | |
| Sample | ml | mg | % | nmoles | nmoles-mg$^{-1}$ protein | % | nmoles | % | nmoles | % |
| 1. Applied on AID-EA (cholate extract of microsomes) | 50.0 | 150.0 | 100 | 27.5 | 0.18 | 100 | 26.5 | 100 | 295.0 | 100 |
| 2. Eluted with buffer | 77.8 | 37.3 | 24.9 | 10.9 | 0.29 | 39.6 | 57.1 | 215.5 | 151.7 | 51.4 |
| 3. Eluted with 0.5 M KCl* | 61.3 | 9.6 | 6.4 | 0.9 | 0.10 | 3.3 | 1.4 | 5.3 | 13.0 | 4.4 |
| 4. Eluted with 0.1% Triton N-101 | 67.1 | 2.4 | 1.6 | 0 | 0 | 0 | 0 | 0 | 2.7 | 0.9 |
| 5. Eluted with 0.5% Renex-690 | 87.4 | 6.0 | 4.0 | 0 | 0 | 0 | 0 | 0 | 6.9 | 2.3 |
| Total Recovery (%) | | | 36.9 | | | 42.9 | | 220.8 | | 59.0 |

*KCl and detergents are dissolved in "buffer" (50 mM potassium phosphate pH 7.3 containing 20% glycerol); colume size 1.5 × 10 cm.
+Microsomes, before Sephadex G-10, contained 0.57 nmoles P-448 and 0.06 nmoles P-420 per mg protein, respectively.

Table II shows a 60-fold purification of P-448 with a 74% yield after a single passage through the column which contains the polymer treated with both the benzo[a]pyrene analog and monoethanolamine (AID-BP). Calculated from starting microsomes P-448 purification is more than 10-fold with an overall yield 17%. It should be noted that Renex-690 (a nonionic detergent similar to Triton-N101) cannot be itself elute P-448. This unexpected two-detergent requirement for elution may be due to the fact that the polymer binds small hydrophobic molecules (polycyclic hydrocarbons and steroids, polyamines, etc.) and non-ionic detergents (the UV-absorption of the first P-448 fractions is 10-20% of that of the applied Triton and Renex-buffers).

One-fourth of the applied P-448 (and the bulk of "elutable" P-420) does not bind to the polymer. This is not due to overloading of the column because the same fraction of P-448 is eluted with buffer when half as much P-448 is applied. It probably results from the fact that either a different kind of P-448 or endogenous "ligands" such as small molecules, proteins, or tightly bound cholate diminish its affinity for the polymer. The quantitative recovery of P-448 from the AID-BP column is interpreted to means that immobilized BP (substrate) stabilizes P-448 and shows that such aminimide polymers are most suitable for affinity chromatography of acidic proteins (all known components of the P-448 mono oxygenase have pI values between 4.3-5.6 as determined by slab isoelectric focusing electrophoresis).

Table II.
Purification of P-448* (Extracted by Cholate from Microsomes) on the AID-BP Column

| Sample | Volume ml | Protein mg | Protein % | Cytochrome P-448ψ nmoles | Cytochrome P-448ψ nmoles·mg$^{-1}$ protein | Cytochrome P-448ψ % | P-420ψ nmoles | P-420ψ % | Protoheme (pyridine hemochromogen) nmoles | Protoheme (pyridine hemochromogen) % |
|---|---|---|---|---|---|---|---|---|---|---|
| 1. Applied on AID-BP | 75.0 | 495.0 | 100 | 64.0 | 0.13 | 100 | 207.0 | 100 | 307.0 | 100 |
| 2. Eluted with buffer | 186.0 | 58 | 11.7 | 17.6 | 0.30 | 27.5 | 49.0 | 123.6 | 98.8 | 32.2 |
| 3. Eluted with 0.5M-KCl+ | 78.9 | 4.3 | 0.9 | 0.6 | 0.14 | 0.9 | 0.9 | 0.4 | 1.5 | 0.5 |
| 4. Eluted with 0.1% Triton N-101 | 77.7 | 1.8 | 0.4 | 0 | 0 | 0 | 0 | 0 | 0 | 0 |
| 5. Eluted with 0.5% Renex-690 | | | | | | | | | | |
| a. First peak | 87.5 | 4.3 | 0.9 | 35.0 | 8.14 | 55.0 | 8.2 | 4.0 | 73.0 | 24.0 |
| b. Second peak | 87.3 | 1.5 | 0.3 | 12.4 | 8.27 | 19.0 | 0 | 0 | 35.5 | 12.0 |
| Total Recovery (%) | | | 14.2 | | | 105.6 | | 28.0 | | 68.2 |

*Different batch from that used in Table 1; column was covered with black cloth.
$^{30}$KCl and detergents are dissolved in "buffer" (50 mM potassium phosphate pH 7.3 containing 20% glycerol).
ψMicrosomes, before Sephadex G-10, contained 0.6 nmoles P-448 and 0.06 nmoles P-420 per mg protein, respectively, P-448 yield from starting microsomes to step 1 above was 24%.

Benzo[a]pyrene Metabolism

P-448 fractions eluted from the benzo[a]pyrene column were tested for their catalytic activity towards benzo[a]pyrene. (Table III, experiments 1, 3, 5 and 7) and the metabolites of BP formed were separated by high pressure liquid chromatography (HPLC) and quantitated radio-chemically. Prior to incubation, the [$^{14}$C]BP used in these experiments was purified by HPLC from BP metabolites (mainly quinones) which had been produced during storage, in the dark, of stock BP-dioxane solution.

Table III.
Metabolism of benzo[a]pyrene by Reconstituted Liver P-448 Monooxygenase in the Presence or Absence of UDPG

| Experiment | Source of P-448 | Metabolized (%) | UDPG | Diol 1 | Diol 2 | Diol 3 | Quinone 1 & 2 | Phenol 1 | Phenol 2 | Phenol 1 Phenol 2 |
|---|---|---|---|---|---|---|---|---|---|---|
| 1 | Cholate extract of microsomes | 4.6 | − | 6.8 | 3.2 | 6.4 | 18.8 | 29.6 | 35.0 | 1:1.2 |
| 2 | | 2.8 | + | 9.7 | 4.0 | 8.1 | 12.0 | 16.0 | 50.2 | 1:3.1 |
| 3 | Buffer-eluate from AID-BP column | 12.7 | − | 13.0 | 6.3 | 10.5 | 24.8 | 30.1 | 15.3 | 1:0.5 |
| 4 | | 9.5 | + | 21.8 | 11.0 | 15.3 | 8.0 | 23.8 | 20.1 | 1:0.8 |
| 5 | First peak of Renex-eluate from AID-BP column | 6.2 | − | 4.8 | 2.1 | 5.3 | 20.4 | 26.4 | 40.8 | 1:1.6 |
| 6 | | 3.0 | + | 9.7 | 3.6 | 7.0 | 15.9 | 22.0 | 41.7 | 1:1.9 |
| 7 | Second peak of Renex-eluate from AID-BP column | 4.2 | − | 4.8 | 1.7 | 4.5 | 18.8 | 30.5 | 39.7 | 1:1.3 |
| 8 | | 1.7 | + | 9.3 | 2.5 | 5.6 | 22.0 | 24.2 | 36.3 | 1:1.5 |

Foot note to Table III
Numbers in each experiment are the percent of each group of metabolites - extracted in the organic phase - expressed as proportion of total radioactivity eluting before benzo[a]pyrene. [Conditions of HPLC: 50°, 350 psig, linear gradient at 3% per min from 30-70% methanol-water; fractions were collected over 30 or 60 sec.]

One ml incubation mixtures contained: 0.2 nmol P-448, 120 unites NADPH cytochrome c reductase, 0.1 mg lipid, 0.5 μmol NADPH, 3μmol MgCl$_2$, 100 μmol potassium phosphate buffer (pH 7.3) and 75-95 nmol HPLC-purified [$^{14}$C]-BP (9750 cpm per nmol BP)dissolved in 0.05 ml acetone; identical amounts of BP were added to each of the two incubation mixtures of every P-448 fraction; 3 μmol UDPG was added as indicated and to experiment 1 50 units (nmol) styrene glycol per min at 37° of purified epoxide hydrase were added. Incubation was at 37° for 10 min and the reaction was stopped with 1 ml acetone and 2 ml ethyl acetate. After mixing for 30 sec. and centrifuging, the organic phase was removed, 1 ml ethyl acetate was layered on the aqueous phase, removed and combined with the rest of organic phase; after removal of solvents at 40° with a stream of nitrogen, the residue was dissolved in 10 μl dioxane and injected in the HPLC column.

Footnote to Table III

Numbers in each experiment are the percent of each group of metabolites—extracted in the organic phase—expressed as proportion of total radioactivity eluting before benzo[a]pyrene. [Conditions of HPLC: 50°, 350 psig, linear gradient at 3% per min from 30-70% methanol-water; fractions were collected over 30 or 60 sec.]

One ml incubation mixtures contained: 0.2 nmol P-448, 120 unites NADPH cytochrome c reductase, 0.1 mg lipid, 0.5 μmol NADPH, 3 μmol $MgCl_2$, 100 μmol potassium phosphate buffer (pH 7.3) and 75–95 nmol HPLC-purified [$^{14}$C]-BP (9750 cpm per nmol BP] dissolved in 0.05 ml acetone; identical amounts of BP were added to each of the two incubation mixtures of every P-448 fraction; 3 μmol UDPG was added as indicated and to experiment 1 50 units (nmol) styrene glycol per min at 37° of purified epoxide hydrase were added. Incubation was at 37° for 10 min and the reaction was stopped with 1 ml acetone and 2 ml ethyl acetate. After mixing for 30 sec. and centrifuging, the organic phase was removed, 1 ml ethyl acetate was layered on the aqueous phase, removed and combined with the rest of organic phase; after removal of solvents at 40° with a stream of nitrogen, the residue was dissolved in 10 μl dioxane and injected in the HPLC column.

EXAMPLE 2

This example illustrates a high pressure liquid chromatography application of the invention.

One and one-half g of the methacrylimide-chloromethyl-styrene-BP polymer (AID-BP) described in Example 1 was dissolved in chloroform and mixed with Zipax glass beads (30.5 g) in a rotating flash for 2–3 hours. The solvent is removed under reduced pressure to yield beads coated with the AID-BP polymer. The dry beads are slowly added to a stirred solution of diethyl ether containing monoethanolamine and triethylamine (10-fold molar excess to —$CH_2$ Cl groups present) which couple the remaining $CH_2Cl$ groups to monoethanolamine and seal the polymer coat on the beads. The resulting polymer coating is insoluble in organic solvents but wettable with water.

The thus coated beads were packed in a standard HPLC stainless steel column (0.8×43 cm). The column was connected to a HPLC (200 psi) and the beads washed with 300 ml of 30% methanol-water at 50° C. The column was then washed with 300 ml of 50 mM phosphate buffer (pH 7.5). The column was then equilibrated at 8° C. with buffer containing 20% glycerol to stabilize the membrane enzymes to be separated.

The HPLC was then used to fractionate the enzyme composition employed in Example 1 (30–50 nanomoles cytochrome P-448 from cholate-extracted rate liver microsomes). Elution was achieved with KCl, detergent solution in glycerol-buffer. Recovery and purification of the enzymes is similar to the gravitational flow system of Example 1. However, the use of the coated glass beads and high pressure liquid chromatography techniques enabled a completion of the experiment in 5 hours as compared to the 2–4 days required by the gravitational system.

It will be apparent that experimental conditions of pressure, temperature, concentration on the polymer of immobilized substrate, etc., can be varied depending upon the nature of the material to be fractionated and/or purified.

The ligand containing polymers of the invention can be employed alone in gravitational flow affinity chromatography systems (Example 1) or they may be coated on suitable supports such as glass beads for use in either gravitational flow or high pressure chromatographic systems (Example 2). The invention provides a new class of absorbent materials for utilization in affinity chromatography systems. One need only modify the copolymer with a suitable binding site ligand to fractionate, separate or purify any mixture. The substrate may be made specific to virtually any component of a mixture by judicious choice of ligand. Although the invention is ideally suited for the separation and/or purification of mixtures of biologically active molecules, it will be apparent to those skilled in the art that the absorbents of the invention may be utilized for the separation of virtually any mixture.

EXAMPLE 3

This example illustrates a method for the preparation of the amine analog of estrone.

4-$^{14}$C-estrone (1.08 μmols) and 2.6 mmols of unlabelled estrone were dissolved in 70 ml of toluene and reacted with 39 mmols of hexamethylenediamine. The reaction mixture is refluxed for 24 hours with 5 mg of toluene sulfonic acid catalyst. A 5 Å molecular sieve is used to remove water. The product is washed vigorously to remove excess diamine and then washed with chloroform and ethyl ether. The product was verified by infrared spectrophotometry (C=N stretch at 6.0 μm) and by thin layer chromatography employing as a solvent 90:10=benzene-methanol. The product was also tested for primary amine groups with ninhydrin spray and with fluorescamine spray. The yield was 25%. The product was found to have the structure:

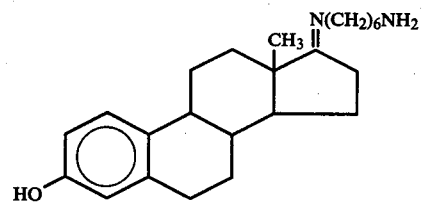

The process was repeated using ethylenediamine to prepare the corresponding ethylenediamine analog of estrone.

EXAMPLE 4

This example illustratez a method for the preparation of 4-[N-imidazoyl]-benzylamine.

(a) Preparation of 4-[N-imidazoyl]benzonitrile 30 mmoles of [2-$^{14}$C] imidazole were dissolved in 2.5 ml chloroform and mixed with 18 ml dimethylformamide containing 30.2 mmoles of p-fluorobenzonitrile and 3.2 g $Na_2CO_3$. The mixture was stirred at 125° C. for three days [Johnson, J. Med. Chem., Vol. 12, p. 1024 (1969)]. The product was isolated and recrystallized twice from benzene: hexanes (1:1). Yield 48%; mp 152°–154°; elemental analysis: found: 70.85% C, 4.13% H and 24.81% N; theoretical: 70.99% C, 4.17% H and 24.84% N.

(b) Preparation of benzyl amine

Sodium-bis(2-methoxyethoxy) aluminum hydride was employed to reduce the above nitrile in toluene according to the method of Bazant et al., Tetrahedron Letters, (1968), p. 3303. After a 4-hour reflux the reaction mixture was cooled and water added. The organic phase was separated and the water phase extracted continuously for 20 hours with benzene. Thin layer chromatography of the combined organic phases on alumina sheets using as solvent benzene-methanoltriethylamine (94:5:1) gave three spots. The spot at the origin had 75% of the $^{14}$C-counts and gave a positive primary amine test with the fluorescamine spray, (starting nitrile, imidazole and benzylamine have $R_5$ values of 0.66, 0.09 and 0.37, respectively.

What is claimed is:

1. A polymer suitable for use in affinity chromatography comprising an addition copolymer of (1) at least one aminimide of the structural formula:

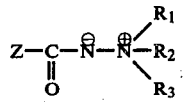

wherein
- $R_1$ and $R_2$ are the same or different and represent lower alkyl;
- $R_3$ represents an organic group, and
- Z represents the residue of a polymerizable vinyl compound, and (2) a vinyl compound having at least one pendant primary halomethyl group.

2. The polymer of claim 1 wherein said aminimide is 1,1-dimethyl-1-(2-hydroxyoctyl)amine methacrylimide and said vinyl compound is a chloromethyl styrene.

* * * * *

UNITED STATES PATENT AND TRADEMARK OFFICE
CERTIFICATE OF CORRECTION

PATENT NO. : 4,162,355
DATED : July 24, 1979
INVENTOR(S) : John C.M. TSIBRIS

It is certified that error appears in the above-identified patent and that said Letters Patent is hereby corrected as shown below:

Column 1, line 6, insert the following paragraph:

-- Research leading to the conception and reduction to practice of the invention claimed herein was supported in part by Grant No. AM-16038 issued by the National Institutes of Health. The United States Government has certain rights in and to the claimed invention. --

Signed and Sealed this

Fourth Day of April, 1995

Attest:

BRUCE LEHMAN

Attesting Officer

Commissioner of Patents and Trademarks